United States Patent [19]
Cincotta et al.

[11] Patent Number: 5,830,895
[45] Date of Patent: *Nov. 3, 1998

[54] METHODS FOR THE DETERMINATION AND ADJUSTMENT OF PROLACTIN DAILY RHYTHMS

[75] Inventors: Anthony H. Cincotta, Andover, Mass.; Albert H. Meier, Baton Rouge, La.

[73] Assignees: The Board of Supervisors of Louisiana State University and Agricultural and Mechanical College, Baton Rouge, La.; Ergo Research Corporation, Wakefield, R.I.

[ * ] Notice: The term of this patent shall not extend beyond the expiration date of Pat. No. 5,585,347.

[21] Appl. No.: 456,952

[22] Filed: Jun. 1, 1995

Related U.S. Application Data

[60] Division of Ser. No. 264,558, Jun. 23, 1994, abandoned, which is a continuation-in-part of Ser. No. 995,292, Dec. 22, 1992, Pat. No. 5,585,347, Ser. No. 178,569, Jan. 7, 1994, and Ser. No. 171,897, Dec. 22, 1993, abandoned, which is a continuation-in-part of Ser. No. 995,292, Dec. 22, 1992, Pat. No. 5,585,347, which is a continuation-in-part of Ser. No. 719,745, Jun. 24, 1991, Pat. No. 5,344,832, which is a continuation-in-part of Ser. No. 463,327, Jan. 10, 1990, abandoned, which is a continuation-in-part of Ser. No. 192,332, May 10, 1988, abandoned.

[51] Int. Cl.[6] ................................. A61K 38/00
[52] U.S. Cl. .............. 514/250; 436/63; 436/71; 436/87; 436/811; 514/12; 514/288; 514/866; 514/338; 514/909
[58] Field of Search ................. 436/71, 87, 11, 436/63; 514/250, 288, 866, 338, 909, 12

[56] References Cited

U.S. PATENT DOCUMENTS

| 4,219,555 | 8/1980 | Rucman | 525/132 |
|---|---|---|---|
| 4,239,763 | 12/1980 | Milavec | 514/250 |
| 4,657,932 | 4/1987 | Martin et al. | 514/665 |
| 4,659,715 | 4/1987 | Meier et al. | 514/288 |
| 4,749,709 | 6/1988 | Meier | 414/399 |
| 4,774,073 | 9/1988 | Mendelson | 424/9 |
| 4,783,469 | 11/1988 | Meier et al. | 514/288 |
| 5,006,526 | 4/1991 | Meier et al. | 514/250 |
| 5,344,832 | 9/1994 | Cincotta et al. | 514/288 |
| 5,468,755 | 11/1995 | Cincotta et al. | 514/288 |
| 5,585,347 | 12/1996 | Meier et al. | 514/12 |

FOREIGN PATENT DOCUMENTS

| BE-890-369 | 9/1980 | Japan . |
|---|---|---|
| 2192541 | 7/1988 | United Kingdom . |
| PCT/US92/05074 | 6/1992 | WIPO . |
| PCT/US92/11166 | 12/1992 | WIPO . |

OTHER PUBLICATIONS

Marken et al. "Management of Psychotropic–induced Hyperprolactinemia" Clinical Pharmacy, vol. 11, Oct. 1992, pp. 851–855.

Iranhanesh et al. "Attenuated Pulsatile Release of Prolactin in Men w/Insulin–Dependent Diabetes Mellitus" Journal of Clinical Endocrinology and Metabolism. vol. 71, 1, 73–78, 1990.

Barnett et al. "Effect of Bromocriptine on Maturity Onset Diabetes" Postgraduate Medical Journal (Jan. 1980) pp. 11–14.

Meier et al. Timed Bromocriptine Administration Reduces Body Fat Stores in Obese Subjects & Hyperglycemia in type II diabetes; Experientia 48 (1992) pp. 249–253.

(List continued on next page.)

Primary Examiner—Jill Warden
Assistant Examiner—Sharidan Carrillo
Attorney, Agent, or Firm—Darby & Darby

[57] ABSTRACT

Methods for detecting abnormalities in prolactin daily rhythms of a subject are provided. Prolactin levels of a subject are compared to levels of healthy subjects and based on the comparison a determination is made of the adjustments necessary to normalize the subject's daily prolactin rhythm. Also provided are methods for normalizing a subject's daily prolactin rhythm.

49 Claims, 4 Drawing Sheets

OTHER PUBLICATIONS

Eismann et al. "Evaluation of a Role for Prolactin in Growth and the Photoperiod–induced Growth Response in Sheep". Journal of Animal Science, 59, 1, 1984, 86–94.

Meier et al. "Temperature–induced Phase Shift of Daily Rhythm of Serum Prolactin in Gulf Killifish" Nature, vol. 271, Feb. 2, 1978 pp. 469–471.

Gnudi et al. "Varieation of Blood Glucose & Serum Growth Hormone, Prolactin & Insulin in Subjects w/ Insulin–Dependent Diabetes, After OGTT & Pretreatment with 2–Bi–δ–Ergocryptine" Acta Diabetologica Latine, vol. 14, 1977, 119–128.

Burns et al., *Chronopharmacology and Chronotherapeutics, Int'l Symp. on Chronopharm. and Chronother.*, Florida A&M University, 1978.

Emata et al., *J. Exp. Zool.*, 273:29–34, 1985.

Komorowski et al., *Aliment. Nutr. Metab.* 1(4): 293, 1980.

Larsson et al., *Lakartidningen (Sweden)*, 82(50):4425, 1985.

Martin, D., "Hormonal Regulation of Migratory Orientation in the White–Throated Sparrow, *Zonatrichia Albicollis*." Diss. LSU, 1974.

Martin, D., "Factors Influencing the Circadian Rhythm of Locomotor Activity in the Anabatoid Fish, *Trichogaster Trichopterus Sumatranus*." Thesis. Sam Houston State College, 1969.

Meier, *Gen & Comp Endocrinol.*, Supp. 3:499–508, 1972.

Meier, *Gen & Comp Endocrinol.*, 26:253–258, 1975.

Meier et al., *Current Ornithology*, 2:303–343, 1984.

Bartness et al., *J. Exp. Zoology* 244:437–454, 1987.

Berle, *Acta Endocrin. Suppl.* 173, Abstract No. 104, 1973.

Burns, et al., *Rev. Chronopharmacology* 5:57–60, 1988.

Chemical Abstacts, vol. 109, No. 9, 66888w, Aug. 29, 1988.

Cincotta, et al., *Amer. J. of Physiol.* 285–93, Feb. 1993.

Cincotta et al., *Ann Nutr Metab* 33:305–14, 1989.

Cincotta et al., *Experientia* 43:416–417, 1987.

Cincotta et al., *Horm. Metabol. Res.* 21:64–68, 1989.

Cincotta et al., *J. Endocrin.* 103:141–146, 1984.

Cincotta et al., *J. Endocrin.* 106:173–176, 1985.

Cincotta et al., *J. Endocrin.* 106:177–181, 1985.

Cincotta et al., *J. Endocrin.* 120:385–391, 1989.

Cincotta et al., *Life Sciences* 45:2247–2254, 1989.

Eisemann et al., *J. of Animal Sci.* 59(1)95–104, 1984.

Haisenleder et al., *Proc. Soc. Exper. Biol. Med.* 187:341–7, 1988.

Horseman et al., *General and Comparative Endocrin.* 38:269–274, 1979.

Horseman et al., *J. Endocrin.* 82:367–372, 1979.

Joseph et al., *J. Exp. Zool.* 178(1):59–62, 1971.

Landgraf et al., *Proc. German Med. Soc.* 82nd Convention, Part II, Apr. 25–29, 1976.

Lee et al., *J. of Exp. Zool.* 166(3):307–316, 1969.

Marken et al., *Clin. Pharmacy* 11:851–5, 1992.

Martin et al., *Neuroendocrinology* 52: 9–14, 1990.

Martin et al., *The Condor* 75: 369–374, 1973.

Meier, *Amer. Scientist* 61(2)184–187, 1973.

Meier, *Amer. Zoology*, 15:905–916, 1975.

Meier et al., *Amer. J. of Physiology* 232(2):E193–E196, 1977.

Meier et al., *Amer. Zool.* 16:649–659, 1976.

Meier et al., *Compar. Endocrin.* 141–44, 1978.

Meier et al., *Science* 173: 1240–42, 1971.

Meier, *Gen. & Comp. Endocrin. Supp.* 2:55–62, 1969.

Meier et al., *Gen. & Comp. Endocrin.* 17: 311–8, 1971.

Meier et al., *Gen. & Comp. Endocrin.* 8(1):110–114, 1967.

Southern et al., *J. Anim. Sci.* 68:931–936, 1990.

Spieler et al., *Gen. & Comparative Endocrin.* 29:156–160, 1976.

Spieler et al., *Life Sciences* 22:255–258, 1977.

Spieler et al., *Nature* 271:469–471, 1978.

Thomas et al., *Semaine des Hopitaux de Paris* 53(34–35): 1857–1862, 1977.

Wheeland, et al., *Comp. Biochem. Physiol.* vol. 53B; 379–385, 1976.

Wilson et al., *Chronobiology Int'l* 6(2):113–121, 1989.3:189–195, 1989.

Meier et al., *Nature* 271:469–471, 1978.

METHODS FOR THE DETERMINATION AND ADJUSTMENT OF PROLACTIN DAILY RHYTHMS

RELATED APPLICATIONS

This application is (i) a division of application Ser. No. 08/264,558, filed Jun. 23, 1994, (now abandoned), which is a continuation-in-part of application Ser. No. 07/995,292, filed Dec. 22, 1992, (now U.S. Pat. No. 5,585,347; and (ii) a continuation-in-part of copending application Ser. No. 08/178,569, filed Jan. 7, 1994; and (iii) a continuation-in-part of application Ser. No. 08/171,897, filed Dec. 22, 1993, (now abandoned in favor of Rule 62 continuation application Ser. No. 08/600,467 now abandoned), which is in turn a continuation-in-part of application Ser. No. 07/995,292, filed Dec. 22, 1992, now U.S. Pat. No. 5,585,347, which is a continuation-in-part of application Ser. No. 07/719,745 filed Jun. 24, 1991 (now U.S. Pat. No. 5,344,832), which is a continuation-in-part of application Ser. No. 07/463,327, filed Jan. 10, 1990 (now abandoned) which is a continuation-in-part of application Ser. No. 07/192,332 filed May 10, 1988 (abandoned in favor of Rule 62 continuation application Ser. No. 07/999,685, filed Dec. 31, 1992, abandoned in favor of Rule 62 continuation application Ser. No. 08/287,066, now U.S. Pat. No. 5,496,803).

All of the foregoing prior applications are in the name of Anthony H. Cincotta and Albert H. Meier, except for Ser. No. 08/171,897 which also names S. L. Tigner, C. E. Runice, and C. L. Pelloni as additional co-inventors.

FIELD OF THE INVENTION

This invention relates to improved methods for the reduction in a subject, vertebrate animal or human, of body fat stores, and reduction of at least one of insulin resistance, hyperinsulinemia, hyperlipidemia, hyperglycemia, and other metabolic diseases, especially those associated with Type II diabetes. In particular the present invention is directed to methods for: (i) normalizing the daily prolactin rhythms of a human or vertebrate animal; (ii) diagnosing aberrant daily prolactin rhythms of a human or vertebrate animal; and (iii) determining the appropriate adjustments that need to be made to normalize such aberrant prolactin rhythms. Such adjustments include the daily administration to the subject of at least one of a prolactin stimulator and/or a prolactin inhibitor at a predetermined time of day (if only one is administered) or at different predetermined times of day (if both are administered). This therapy typically results in the long-term adjustment of aberrant or abnormal prolactin rhythms so that they conform to or simulate normal prolactin cycles, at which point the therapy may be discontinued, while the adjustment permits.

This invention is also directed to improved methods for adjusting the neural oscillator (or oscillators) of which the daily prolactin rhythm is an expression or marker.

The adjustment of daily prolactin rhythms and the daily rhythms of key neural oscillators results in reduction and control over an extended time period of various metabolic or other disorders.

BACKGROUND OF THE INVENTION

Obesity and Lipid Metabolism Disorders

Body Fat Stores

In humans obesity can be defined as a body weight exceeding 20% of the desirable body weight for individuals of the same sex, height and frame (Salans, L. B., in *Endocrinology & Metabolism,* 2d Ed., McGraw-Hill, New York 1987, pp. 1203–1244; see also, R. H. Williams, *Textbook of Endocrinology,* 1974, pp. 904–916). In other animals (or also in humans) obesity can be determined by body weight patterns correlated with prolactin profiles given that members of a species that are young, lean and "healthy" (i.e., free of any disorders, not just metabolic disorders) have daily plasma prolactin level profiles that follow a regular pattern with little or no standard deviation.

Obesity, or excess fat deposits, correlate with and may trigger the onset of various lipid metabolism disorders, e.g. hypertension, Type II diabetes, atherosclerosis, etc.

Even in the absence of clinical obesity (according to the above definition) the reduction of body fat stores (notably visceral fat stores) in man especially on a long-term or permanent basis would be of significant benefit, both cosmetically and physiologically.

The reduction of body fat stores in domestic animals (as well as pets) especially on a long-term or permanent basis would also obviously be of considerable economic benefit to man, particularly since farm animals supply a major portion of man's diet; and the animal fat may end up as de novo fat deposits in man.

Whereas controlled diet and exercise can produce modest results in the reduction of body fat deposits, prior to the cumulative work of the present inventors (including the prior co-pending patent applications and issued U.S. patents referred to below), no truly effective or practical treatment had been found for controlling obesity or other lipid metabolism disorders.

Hyperlipoproteinemia is a condition in which the concentration of one or more of cholesterol- or triglyceride-carrying lipoproteins (such as chylomicrons, very low density lipoproteins or VLDL and low-density lipoproteins or LDL) in plasma exceeds a normal limit. This upper limit is generally defined as the ninety-fifth percentile of a random population. Elevated levels of these substances have also been positively correlated with atherosclerosis and the often resulting cardiac infarction, or "heart attack", which accounts for approximately one-half of all deaths in the United States. Strong clinical evidence has been presented which correlates a reduction in plasma lipoprotein concentration with a reduced risk of atherosclerosis (Noma, A., et al., *Atherosclerosis* 49:1, 1983; Illingworth, D. and Conner, W., in *Endocrinology & Metabolism,* McGraw-Hill, New York 1987). Thus, a significant amount of research has been devoted to finding treatment methods which reduce levels of plasma cholesterol and triglycerides.

Another subset of the plasma lipoproteins found in vertebrates are high density lipoproteins, or HDL. HDL serve to remove free cholesterol from the plasma. A high HDL concentration as a percentage of total plasma cholesterol has been associated with a reduced risk of atherosclerosis and heart disease. Thus HDL are known in the lay press as "good" cholesterol. Therefore, therapeutic strategies involve attempts both to reduce plasma LDL and VLDL content (that is, reduce total plasma cholesterol), and to increase the HDL fraction of total plasma cholesterol. Several lines of research indicate that simply increasing HDL is of benefit even in the absence of LDL or VLDL reduction: Bell, G. P. et al., *Atherosclerosis* 36:47–54, 1980; Fears, R., *Biochem. Pharmacol.* 33:219–228, 1984; Thompson, G., *Br. Heart J.* 51:585–588, 1989; Blackburn, H. *N.E.J.M.* 309:426–428, 1983.

Current therapies for hyperlipoproteinemias include a low fat diet and elimination of aggravating factors such as sedentary lifestyle. If the hyperlipoproteinemia is secondary (i.e. incident to e.g. a deficiency of lipoprotein lipase or LDL receptor, various endocrine pathologies, alcoholism, renal disorders, hepatic disorders) then control of the underlying disease is also central to treatment. Hyperlipoproteinemias are also treated with drugs, which usually alter the levels of particular components of the total plasma cholesterol, as well as reduce the total plasma lipid component. Among the recently introduced drugs to treat hyperlipoproteinemia is lovastatin (MEVACOR®) which selectively inhibits an enzyme involved in cholesterol production, 3-hydroxy-3-methylglutaryl coenzyme A (HMG-CoA) reductase. This drug specifically reduces total cholesterol and can cause a modest (5–10%) increase in HDL concentrations. However, benefits from these therapies vary from subject to subject.

Moreover, use of the HMG-CoA enzyme inhibitor is sometimes accompanied by side effects such as liver toxicity, renal myoglobinuria, renal shutdown, and lenticular opacity. The risk of such side effects necessitates close monitoring of the patients (e.g., liver function is tested monthly).

Another drug prescribed against hyperlipoproteinemia is clofibrate. The effectiveness of clofibrate also varies from subject to subject and its use is often accompanied by such side effects as nephrotic syndromes, myalgia, nausea and abdominal pain.

Diabetes

Diabetes, one of the most insidious of the major diseases, can strike suddenly or lie undiagnosed for years while attacking the blood vessels and nerves. Diabetics, as a group, are far more often afflicted with blindness, heart disease, stroke, kidney disease, hearing loss, gangrene and impotence. One third of all visits to physicians are occasioned by this disease and its complications, and diabetes and its complications are a leading cause of untimely death in the United States and in the Western world.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally converted in the liver to $CO_2$ and $H_2O$ (50%); to glycogen (5%); and to fat (30–40%), the latter being stored in fat depots. Fatty acids from the adipose tissues are circulated, returned to the liver for re-synthesis of triacylglycerol and metabolized to ketone bodies for utilization by the tissues. The fatty acids are also metabolized by other organs. Fat formation is a major pathway for carbohydrate utilization.

The net effect of insulin is to promote the storage and use of carbohydrates, protein and fat. Insulin deficiency is a common and serious pathologic condition in man. In insulin-dependent (IDDM or Type I) diabetes the pancreas produces little or no insulin, and insulin must be injected daily for the survival of the diabetic. In noninsulin-dependent (NIDDM or Type II) diabetes the pancreas retains the ability to produce insulin and in fact may produce higher than normal amounts of insulin, but the amount of insulin is relatively insufficient, or less than fully effective, due to cellular resistance to insulin.

In either form of diabetes there are widespread abnormalities. In most NIDDM subjects, the fundamental defects to which the abnormalities can be traced are (1) a reduced entry of glucose into various "peripheral" tissues and (2) an increased liberation of glucose into the circulation from the liver. There is therefore an extracellular glucose excess and an intracellular glucose deficiency. There is also a decrease in the entry of amino acids into muscle and an increase in lipolysis. Hyperlipoproteinemia is also a complication of diabetes. The cumulative effect of these diabetes-associated abnormalities is severe blood vessel and nerve damage.

No effective treatment has been found for controlling either hyperinsulinemia or insulin resistance prior to the work of the present inventors. Hyperinsulinemia is a higher-than-normal level of insulin in the blood. Insulin resistance can be defined as a state in which a normal amount of insulin produces a subnormal biologic response. In insulin-treated patients with diabetes, insulin resistance is considered to be present whenever the therapeutic dose of insulin exceeds the secretory rate of insulin in normal persons. Insulin resistance is also associated with higher-than-normal levels of insulin i.e. hyperinsulinemia—when normal or elevated levels of blood glucose are present.

The principal unit of biological time measurement, the circadian or daily rhythm, is present at all levels of organization. Daily rhythms have been reported for many hormones inclusive of the adrenal steroids. e.g., the glucocortico-steroids, notably cortisol, and prolactin, a hormone secreted by the pituitary. In an early article, discussing the state-of-the-art at that time, it was reported that "Although correlations have been made between hormone rhythms and other rhythms, there is little direct evidence that the time of the daily presence or peak level of hormones has important physiological relevance." See *Temporal Synergism of Prolactin and Adrenal Steroids* by Albert H. Meier, General and Comparative Endocrinology. Supplement 3, 1972 Copyright 1972 by Academic Press, Inc. The article reports that the peak concentration of prolactin occurs at different times of day in lean and fat animals. The article then describes avian physiological responses to prolactin injections given daily for several days. These responses include increases and decreases in body fat stores, dependent on the time of day of the injection. Furthermore the time of day when prolactin injections promote loss of body fat coincides with the time of day when prolactin is greatest in lean birds. Additionally, the time when prolactin injections promote gain of body fat coincides with the time when prolactin is greatest in obese birds. Prolactin was thus found to stimulate fattening only when injected at certain times of the day, and time of the response to prolactin was found to differ between lean animals and fat animals.

In an article titled *Circadian and Seasonal Variation of Plasma Insulin and Cortisol Concentrations in the Syrian Hamster, Mesocricetus Auratus* by Christopher J. de Souza and Albert H. Meier, Chronobiology International, Vol. 4. No. 2. pp 141–151, 1987, there is reported a study of circadian variations of plasma insulin and cortisol concentrations in scotosensitive and scotorefractory Syrian hamsters maintained on short and long periods of daylight to determine possible seasonal changes in their daily rhythms. The baseline concentration of insulin was found to be higher in female than in male scotosensitive hamsters on short daylight periods. These differences, it is reported, may account for the observed heavy fat stores in female hamsters kept on short daylight periods. The plasma concentrations of both cortisol and insulin varied throughout the day for the groups of animals tested, but were not equivalent. The circadian variation of insulin and cortisol differed markedly with sex, seasonal condition and day length. Neither the daily feeding pattern or glucose concentration varied appreciably with seasonal condition, or daylight. The time of day, or the season, it is reported, do not appear to affect the concentrations in glucose levels. It is postulated that the daily rhythms of cortisol and insulin are regulated by different neural pacemaker systems, and that changes in the phase relations of circadian systems account in part for seasonal changes in body fat stores. The circadian rhythms of prolactin and the glucocorticosteroid hormones, e.g., cortisol, have thus been perceived as having important though far from fully understood roles in regulating daily and seasonal changes in body fat stores and in the organization and integration of total animal metabolism. See *Circadian Hormone Rhythms in Lipid Regulation* by Albert H. Meier and John T. Burns, Amer. Zool. 16:649–659 (1976).

In our prior co-pending patent application Ser. No. 192,332 (and its Rule 62 continuation application Ser. No. 07/999,685, both abandoned in favor of Rule 62 continuation application Ser. No. 08/287,066, now U.S. Pat. No. 5,496,803) we have disclosed and claimed methods for regulating lipid metabolism disorders by administering prolactin (or both prolactin and a glucocorticosteroid ("GC")) into the bloodstream of an animal or human on a timed daily basis in an amount and for a period of time sufficient to modify and reset the neural phase oscillation of the prolactin daily rhythm which then increases insulin sensitivity. The prolactin (or prolactin and glucocorticosteroid) injections are timed to create a peak in the subject's daily prolactin (or both prolactin and glucocorticosteroid) profile that coincides in time with the peak prolactin (or prolactin and GC peaks, respectively) of a lean, insulin-sensitive human to increase insulin sensitivity and reduce body fat stores. Injections of the same agent(s) are timed towards the peak prolactin time of an obese subject to achieve fat gain, if desired.

In our co-pending prior application Ser. No. 463,327 (abandoned in favor of its Rule 62 continuation application Ser. No. 07/719,745, now U.S. Pat. No. 5,344,832) (and its continuation-in-part Ser. No. 07/813,125 abandoned in favor of its Rule 62 continuation application Ser. No. 08/158,153, now U.S. Pat. No. 5,468,755) we have disclosed and claimed a method of modifying and resetting the neural phase oscillations of the brain which controls both prolactin and GC in an obese animal (or human) by administering a dopamine agonist at a predetermined time of day such that the prolactin (and/or GC) peak(s) of the obese animal (or human) will be phase-shifted to occur at the time that it occurs (they occur) in a lean animal (or human), with the result that at least one of body fat stores, body weight, hyperinsulinemia, or hyperglycemia will be reduced and/or insulin sensitivity will be increased.

In our co-pending prior application Ser. No. 719,745 (now U.S. Pat. No. 5,344,832) we have disclosed and claimed enhanced methods for modifying and resetting the neural phase oscillations of the brain which control prolactin levels comprising both (a) administering to the subject a dopamine agonist just after the time at which the normal prolactin profile peaks to reduce prolactin levels to the low "day" levels and (b) administering to the subject a prolactin stimulator at a time just before the prolactin level peaks in normal subjects with the objective of causing the subject's prolactin profile to mimic in shape and time the profile of a lean human not suffering from one or more of aforementioned metabolic disorders.

Ser. No. 719,745 (now U.S. Pat. No. 5,344,832) also discloses and claims the further administration of a thyroid hormone to subjects that are being treated with the dopamine agonist and prolactin stimulator, especially to those subjects that are chronically or seasonally hypothyroid.

In co-pending application Ser. No. 995,292 (now U.S. Pat. No. 5,585,347), we have disclosed and claimed certain improved methods for diagnosing aberrant prolactin rhythms, determining adjustments to be made to abnormal prolactin rhythms, and normalizing abnormal prolactin rhythms.

In co-pending application Ser. No. 171,897 (now abandoned in favor of Rule 62 continuation application Ser. No. 08/600,467 now abandoned), we disclose and claim an accelerated release composition containing a prolactin inhibitor that is quickly released into the blood stream of the subject.

In co-pending application Ser. No. 178,569, we disclose and claim a method of treating various lipid metabolism disorders involving the synergistic combination of diet and the administration of a prolactin inhibitor.

Various aspects of the present invention have not been claimed in the foregoing applications. In addition, various improvements to and advantageous refinements of the administration protocol and its determination have now been made which increase the effectiveness of the treatment.

SUMMARY OF THE INVENTION

One aspect of this invention relates to a method for normalizing the daily prolactin profile of a first vertebrate subject in need of such treatment which comprises the steps of:

comparing the prolactin profile of the first vertebrate subject to the prolactin profile of other vertebrate subjects having a normal prolactin profile; and adjusting the prolactin profile of the first vertebrate subject to cause the profile of said first subject to generally conform to (or simulate) the prolactin profile of said second subjects.

A variation of this aspect of the invention involves (a) comparing only a set of at least two (preferably at least 4, typically 4–6) prolactin levels of the first subject measured at time points during at least two (preferably at least three) key intervals of the day to the corresponding prolactin levels of healthy subjects at the same time points during the day, and (b) adjusting the prolactin levels of the first subject to conform to (or simulate) the corresponding healthy prolactin levels.

As an example, prolactin levels of the first subject can be measured at least twice during each of an early morning key interval and an early evening key interval and preferably at least one or preferably at least two additional prolactin levels may be measured during a night interval.

A second aspect of this invention relates to a method for evaluating the daily prolactin profile of a human subject, which comprises the steps of:

(a) comparing the prolactin profile of said subject, said profile having been determined over a continuous 24-hour period, to a predetermined standard prolactin profile for healthy human subjects; and (b) determining whether said human subject has an abnormal daily prolactin profile by ascertaining whether one of the following obtains: (i) at any time point during waking hours the subject's prolactin level is higher than 1 Standard Error of the Mean (SEM) above the mean prolactin level of healthy subjects at the same time point (or of a standard waking hours mean prolactin level or a standard prolactin profile); and (ii) at any time point during sleeptime the subject's prolactin level is lower than 1 SEM below the mean prolactin level of normal (healthy) individuals at the same time point.

Preferably, the time points compared will be actual prolactin measurement points (i.e. the prolactin levels of the subject being tested will be blood prolactin levels and not extrapolations) and, most preferably, the determination will be based on two prolactin measurement points, instead of just one; alternatively, the determination will be preferably based on whether one measured prolactin level is higher than 2 SEM during waking hours, or lower than 2 SEM during sleeptime.

A variation of this second aspect of the invention involves: (a) comparing only a set of at least two prolactin levels of said human (measured at predetermined time points during each of at least two key intervals of the day) to the corresponding prolactin levels (e.g. in a prolactin profile) for healthy humans at the same time points during the day; and (b) determining whether said human subject has an abnormal prolactin profile by ascertaining whether one of the following obtains: (i) at any of said time points that fall during waking hours the subject's prolactin level is higher than 1 SEM above the corresponding mean prolactin level of healthy subjects (or above the corresponding mean level of a standard prolactin profile) at the same time point; and (ii) at any of said predetermined time points that fall during sleeptime, the subject's prolactin level is lower than 1 SEM below the corresponding night time level of healthy subjects (or below the corresponding night time level of a standard prolactin profile) at the same time point.

A third aspect of this invention relates to a method for determining whether adjustment will be required to "normalize" or generally conform to or approach an abnormal prolactin profile or level to a standard (or healthy) prolactin profile or level, the method comprising: (a) collecting a plurality of blood samples from a subject over a continuous time period, the collection of said samples being made at predetermined time intervals (or at predetermined time points) within said time period; (b) assaying the prolactin content of each of said samples; (c) plotting the prolactin content of each of said samples against the time at which said sample was collected during said time period to generate a plurality of data points (i.e. correlating the prolactin content with the time); (d) generating a prolactin profile by connecting (or otherwise fitting a curve through) said data points; and (e) comparing the prolactin profile to a predetermined normal prolactin profile. Steps (c) and (d) together constitute the step of expressing the prolactin content as a function of time to generate the prolactin profile of the subject.

A variation of this third aspect of the invention involves measuring only key prolactin levels to generate the data points, omitting step (d), and, as step (e), comparing each data point to the corresponding prolactin level at the same time point on the predetermined standard prolactin profile, or to a prolactin level of healthy subjects at the same time point.

A fourth aspect of this invention relates to a method for determining adjustments that will cause an abnormal daily prolactin profile of a patient to conform to or approach a normal individual's daily prolactin profile, which comprises: (a) comparing the prolactin profile of the patient to a predetermined standard prolactin profile for healthy (normal) subjects; (b) determining that at least one of the following obtains: (i) the prolactin level of said patient at any time point (preferably any prolactin measurement points, most preferably any two prolactin measurement points) during waking hours exceeds the corresponding prolactin level at the same time point of normal (healthy) individuals by at least 1 Standard Error of the mean (SEM); and (ii) the prolactin level of such patient at any time point (preferably any prolactin measurement point, most preferably any two prolactin measurement points) during sleeptime is below the corresponding prolactin level of normal healthy individuals at the same time point by at least one SEM; (c) determining the time at which to administer at least one member selected from the group consisting of a prolactin inhibitor and a prolactin stimulator to said subject; and (d) selecting the amount of said prolactin stimulator and/or inhibitor to adjust a subject's aberrant prolactin level so that the subject's prolactin profile conforms to or approaches the prolactin profile of normal (healthy) individuals. Again it is preferred that if the determination is based on one prolactin measurement point being aberrant, the variation from the normal profile be at least 2 SEM.

A variation on this fourth aspect of the invention involves making the determination required in step (b) and the selection required in step (d) based on a comparison of key prolactin levels of the patient at predetermined time points during key intervals of the day (or night) with the corresponding "healthy" or "normal" prolactin levels at the same time points.

BRIEF DESCRIPTION OF THE DRAWINGS

The present invention is further described with respect to the annexed drawings in which.

DETAILED DESCRIPTION OF THE INVENTION

All patents, patent applications and literature references cited herein are incorporated by reference in their entirety as if their disclosures were physically present in the present specification. In case of conflict, however, the present disclosure controls.

It has recently been discovered that metabolic disorders such as the foregoing are associated with aberrant patterns in the daily levels (and fluctuations) of prolactin and neural oscillators such as those associated with dopamine and serotonin. Healthy (normal) subjects, i.e., lean members of a species not suffering from such metabolic abnormalities have highly predictable daily prolactin profiles, which in humans are characterized by a low and relatively constant prolactin level during the waking hours (day) followed by a sharp rise to a peak during sleep (night) and subsequent more gradual tapering down to the waking hours level by morning. Conversely, "healthy" individuals have prolactin profiles that are at within 1 SEM of the standard prolactin profile M or F of FIG. 1 (depending on whether they are male or female), preferably for at least two prolactin levels measured at different times or within 2 SEM of the standard prolactin profile for at least one measured prolactin level.

In the present context "lean" means not obese and not abnormally underweight. In turn, an obese human is defined as a human whose body weight is over twenty percent above the ideal body weight for a given population (R. H. Williams, *Textbook of Endocrinology*, 1974, pp. 904–916) . An abnormally underweight human is anyone at least 10% below his/her ideal bodyweight. Ideal body weight (IBW) can be determined by using the Metropolitan Life Insurance Company standard age/height/weight charts.

A prolactin profile of a subject is obtained by collecting blood samples from the subject at timed intervals during a consecutive time period (preferably at 1–3 hour intervals over approximately a 12–24 hour period), assaying each blood sample for prolactin content, plotting the time of blood sampling against the quantity of prolactin present in each sample to generate a data point for each sample, and connecting the data points (or otherwise fitting them into a curve) to form the prolactin profile.

Alternatively (for the vast majority of subjects) a set of only a few prolactin levels need be obtained by collecting blood samples from the subject at spaced apart times at least once and preferably at least twice during each of at least two key intervals of a 24-hour period. One such key interval is early morning (06:00–09:00); another is early evening (16:00–20:00). Spaced apart samples may be collected for example at 07:00 and 08:00 during the first interval and at 16:00 and 20:00 during the second interval. It is desirable to collect at least one additional sample at night, during a third interval between 23:00 and 02:00, e.g. at 23:00 or at 24:00. One or more additional optional prolactin measurements can be taken at yet another interval, e.g., a late evening interval from 20:00–23:00. Prolactin levels taken during key intervals will be referred to as "key prolactin levels".

This alternative method is preferred in clinical practice to obtaining 24 hour prolactin profiles for several reasons. First, such a procedure, which avoids overnight hospital or blood center stay, is significantly less costly than 24 hour blood draws. Second, the reduced number of blood samples drawn is preferred by patients as it is significantly less disruptive to their daily schedules. The key prolactin levels are used as indicators of the subject's prolactin profile, and as substitutes thereof.

Although females generally have higher prolactin levels and sharper peaks than males, the shape of the normal prolactin profile for both sexes is qualitatively similar and does not vary appreciably from normal individual to normal individual (of the same sex) within the same species.

By contrast, individuals who suffer from one or more metabolic disorders have aberrant (often highly aberrant) daily prolactin profiles and levels. These prolactin profiles and levels not only differ substantially from the norm but they can also differ from one another.

Figure 4:
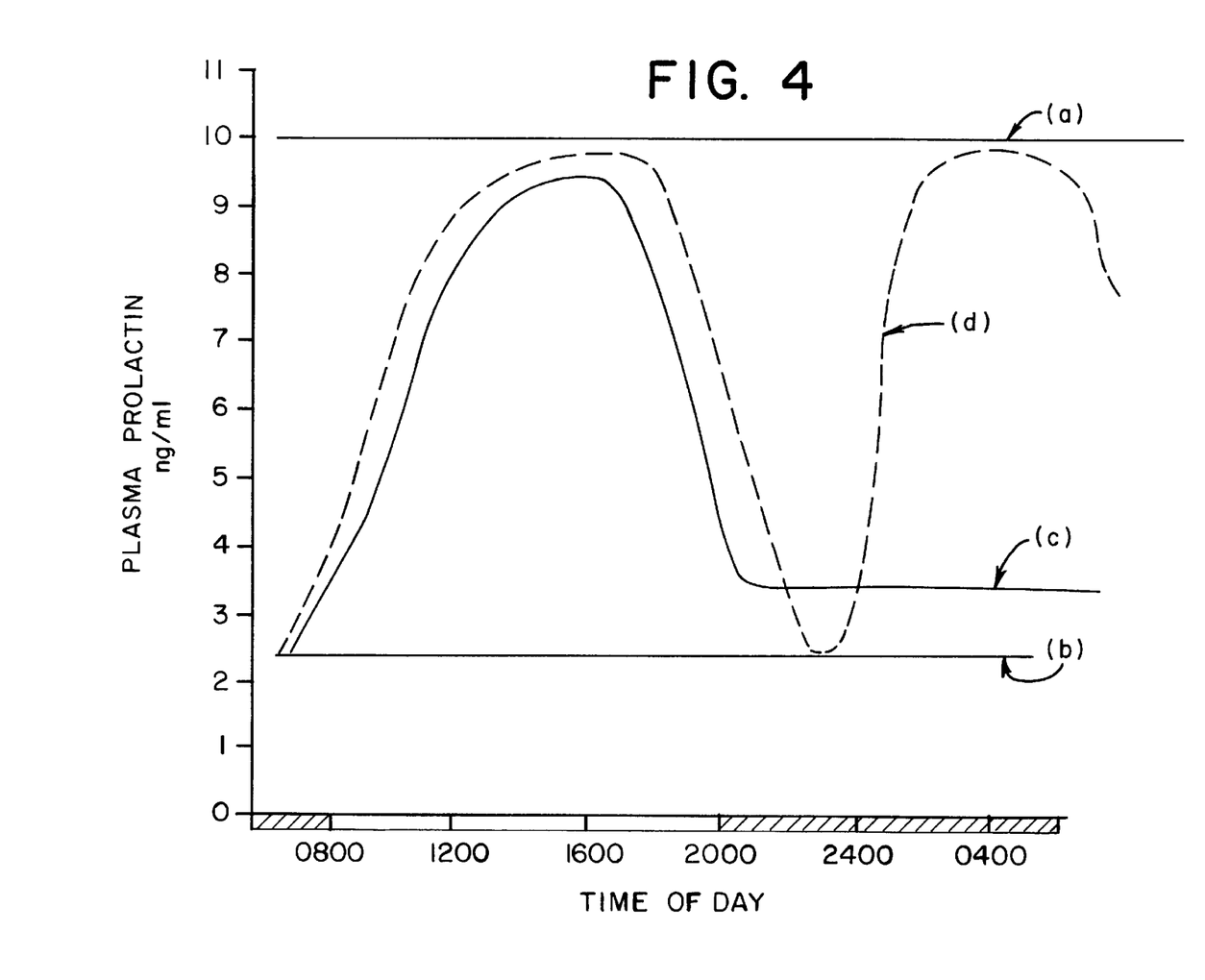
FIG. 4 is an illustrative superimposition of various types of typical human aberrant prolactin profiles (a)–(d).

The vast majority (at least about 80%) of patients with at least one of the foregoing metabolic disorders have abnormal daily prolactin profiles that fall generally in one of four 24-hour patterns represented schematically in FIG. 4:

(a) a flat (peak-free) high level (in this context "high" means higher than the "day" or waking hours prolactin level);

(b) a flat (peak-free) low level (in this context "low" means as low as or lower than the "day" or waking hours prolactin level);

(c) a peak during the "day" and a low level at "night" (in this context, "low" means low as compared to the normal average sleeptime prolactin value between 0100 and 0400); and (d) a peak during the "day" and a second peak at "night".

The alternative method of measuring key prolactin levels in early morning and late evening would diagnose patients with abnormalities of type (a), (c) and (d). If a subject has an abnormal prolactin profile of type (b) above, that subject would have to give one or two night blood samples which would not avoid overnight stay at a hospital or blood center.

"Waking hours" or "day" means the period of time at which in normal (healthy) humans (not working night shifts or alternate shifts) prolactin levels are relatively invariant and low (between 07:00 h and 22:00 h).

As employed herein the term "sleeptime" or "night" means the period of time which in normal humans prolactin level rises to a peak (between 01:00 and 04:00) and then tapers off.

The normal average prolactin levels between the hours of 01:00 and 04:00 are between 8.0 and 14.0 nanograms/ml for males and between 14.0 and 26.0 nanograms/ml for females. See FIGS. 1–4.

"Prolactin inhibitor" shall include substances which directly or indirectly inhibit prolactin in a subject (vertebrate animal or human). Nonlimiting examples of prolactin inhibitors include prolactin inhibiting dopamine agonists such as dopamine and certain ergot-related prolactin-inhibiting compounds.

Nonlimiting examples of prolactin inhibiting dopamine agonists are 2-bromo-alpha-ergocriptine; 6-methyl-8 beta-carbobenzyloxy-aminoethyl-10-alpha-ergoline; 8-acylamino-ergolines, are 6-methyl-8-alpha-(N-acyl) amino-9-ergoline and 6-methyl-8 alpha-(N-phenylacetyl) amino-9-ergoline; ergocornine; 9,10-dihydroergocornine; D-2-halo-6-alkyl-8-substituted ergolines, e.g., D-2-bromo-6-methyl-8-cyanomethylergoline; and lisuride. Moreover, the non-toxic salts of the prolactin-inhibiting ergot-related compounds formed from pharmaceutically acceptable acids are also useful in the practice of this invention. Bromocriptine, or 2-bromo-alpha-ergocryptine, has been found particularly useful in the practice of this invention.

"Prolactin stimulator" shall include substances which directly or indirectly stimulate prolactin. Nonlimiting examples of prolactin stimulators include dopamine antagonists such as metoclopramide, haloperidol, pimozide, phenothiazine, domperidone, sulpiride, chlorpromazine and serotonin agonists, i.e., MAO inhibitors, e.g., pargyline, synthetic morphine analogs, e.g., methadone, antiemetics, e.g., metoclopramide, antipsychotics, e.g., estrogens and others, e.g., tryptophan and 5-hydroxy-tryptophan, melatonin, fluoxitane, and dexfenfluoramine. Moreover, the non-toxic salts of the foregoing prolactin stimulating compounds formed from pharmaceutically acceptable acids are also useful in the practice of this invention. Metoclopramide has been found particularly useful in the practice of this invention.

"Prolactin modulator" shall refer to either prolactin stimulators, prolactin inhibitors, or both.

DEVELOPMENT OF THE "NORMAL" PROLACTIN PROFILE AND KEY LEVELS

A statistically significant number of healthy and young (20–35 years of age) humans are selected as follows:

All subjects are healthy and on normal diurnal work/rest schedule (no night guards or other night-shift workers). They are then divided into two different groups according to sex. All subjects must normally sleep between about 23:00 and about 07:00). The individuals are healthy in the sense that they are free of physiologic disorders or pathologies. In particular, they are not obese (based on standard age/size/weight tables); are known to have normal plasma levels of insulin; and are euthyroid i.e., have normal levels of plasma thyroxin, triiodothyronine, free-thyroxin and TSH, and suffer from no malignancies or autoimmune disorders or generically transmitted diseases.

A statistically significant number shall mean at least 3, the smallest sampling number for which statistical formulas generally have any meaning. However, a sampling number of at least 6 is generally preferred (at least 10 is more preferred) because this amount of sampling generally reduces the standard error (SE) of prolactin determinations.

Blood is collected from each subject at 1–3 hour intervals over a 24-hour period and, diurnal plasma levels of -prolactin, total triiodothyronine (T3) total thyroxin (T4), free-T4 and thyroid stimulating hormone (TSH) are measured for each subject for e.g., blood is collected over a 24-hour period at suitable time intervals (e.g., every 1 to 3 hours), typically starting at 10:00 am and finishing the next morning at 8:00 am).

Suitable sampling techniques and assay procedures are well-known to those skilled in the field and can be selected from published procedures, e.g., Linkowski, P. et al., *J. Clin. Endocrinol. Metab.* 61:429–438, 1985; Van Cauter and Copinschi, "Circadian and Episodic Variations", Martinus Nyhoff, The Hague Netherlands, pp. 1–25, 1981.

During sampling, all subjects must consume the same diet and maintain the same sleeptime schedule. Prolactin data are plotted against time of day and a normal prolactin curve is developed including SEM. Mathematical expressions can also be developed to describe the curves and the area under the curves.

Figure 1:
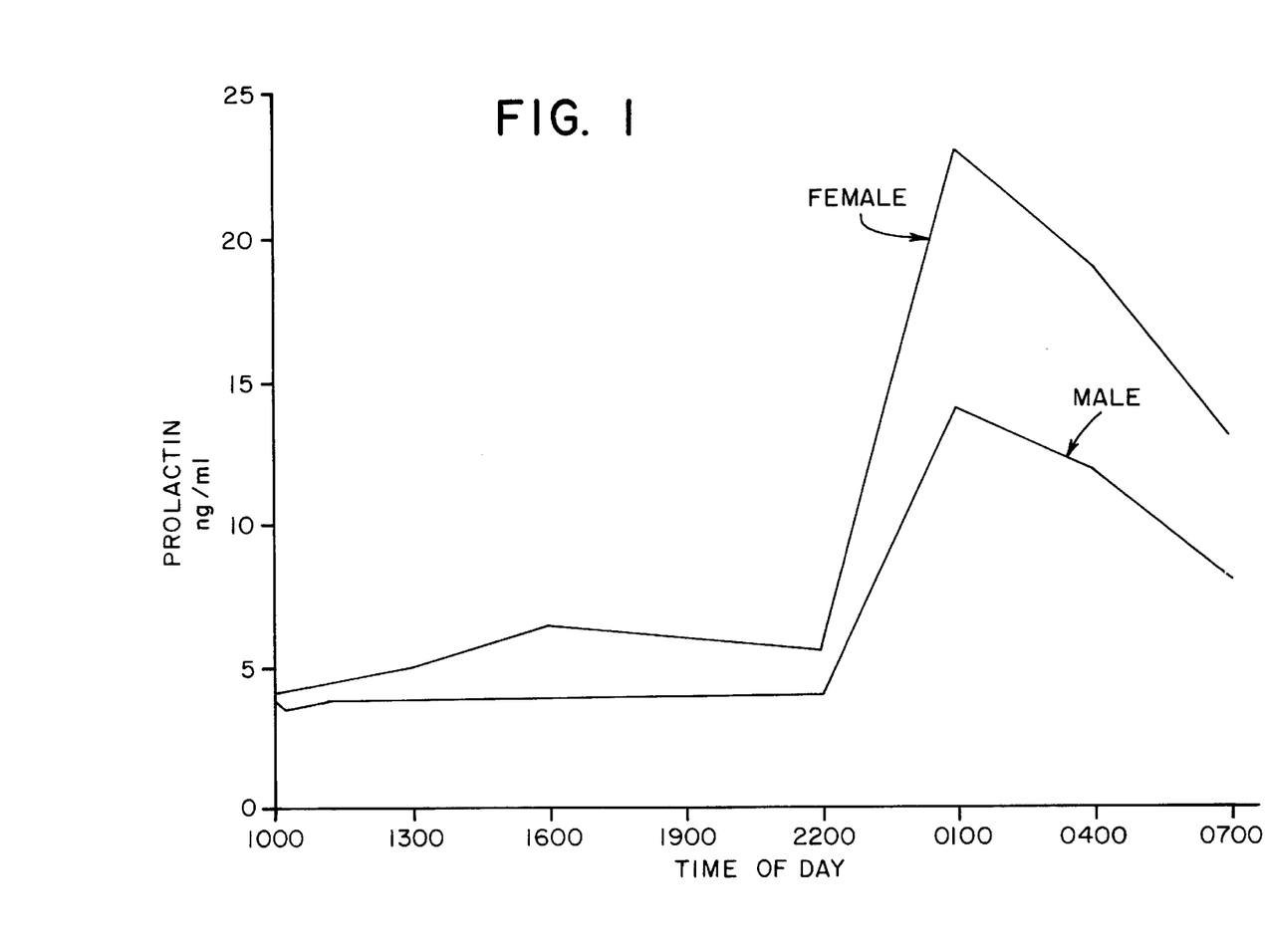
FIG. 1 is a graph of average plasma prolactin levels (ng/ml) for healthy individuals (males: "M" curve; females: "F" curve) v. time of day (hours).
Figure 2:
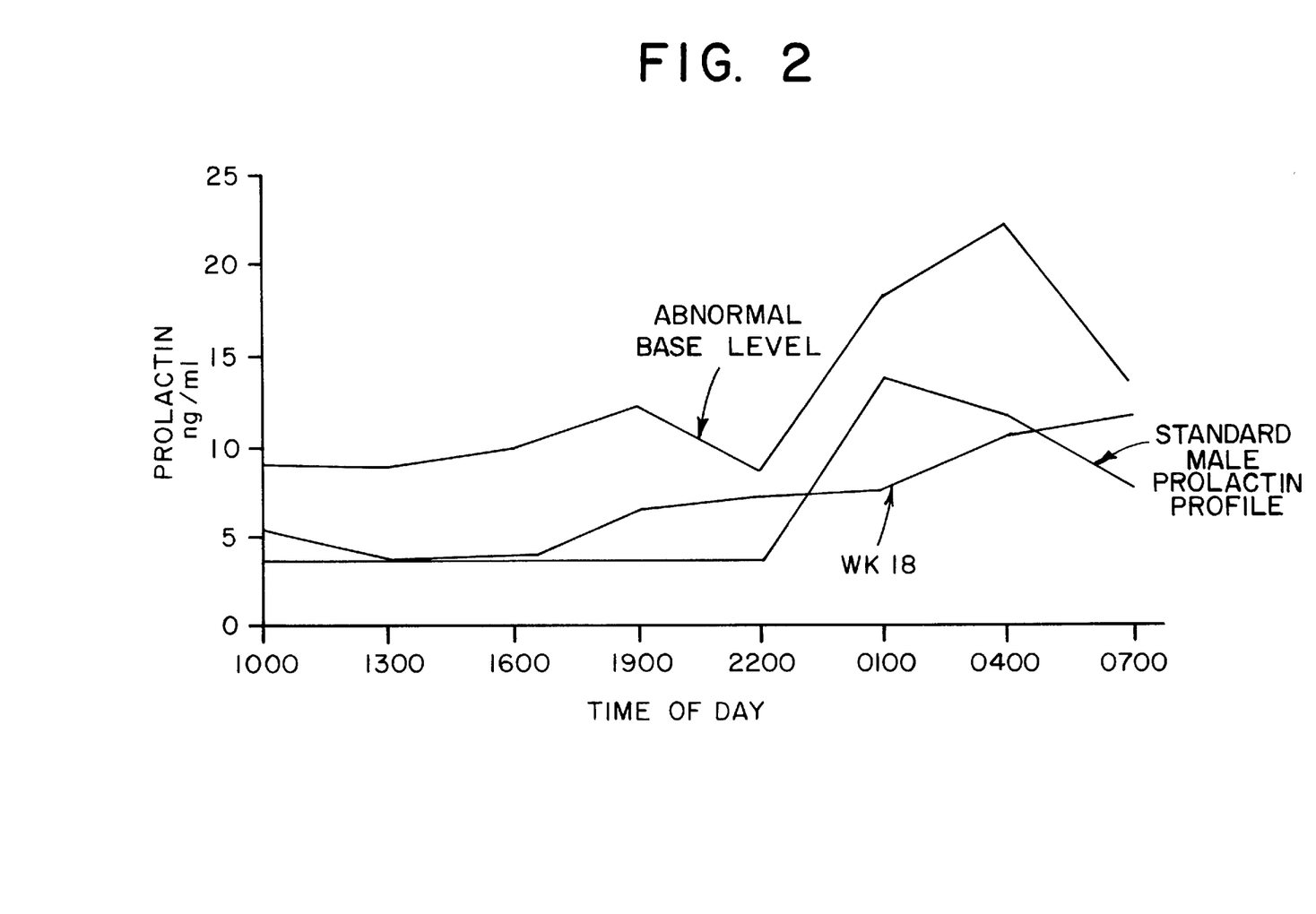
FIG. 2 is a superimposition of a male patient's abnormal base-level (pre-therapy) prolactin profile (thin dotted grey line) and post treatment improved prolactin profile (thin black line), and the standard normal prolactin profile (thick grey line), all in graph form. (Prolactin units are in nanograms per ml, and time of day is in hours.)

The result of a normal 24 hour profile for males approximately 30 years of age is shown as the "M" curve in FIG. 1. The result for females approximately 30 years of age is the "F" curve. The SEM for prolactin during waking hours for males is 1.0 to 2.0 nanograms per ml and approximately 3.0 nanograms per ml during sleeptime. For females the SEM for prolactin during waking hours is between 1.0 and 3.0 nanograms per ml. and between 3.0 and 6.0 nanograms per ml. during sleeptime.

Alternatively, the curves of FIG. 1 can be used as the standard prolactin profile (as well as for the standard prolactin levels at times corresponding to key prolactin measurements); or only a set of prolactin levels can be measured in healthy subjects at key intervals during the day, e.g., at least two in the early morning, at least two in the early evening and optionally one or two at night.

DETERMINATION OF DIURNAL HORMONE PROFILE AND/OR KEY PROLACTIN LEVELS OF "AFFECTED" SUBJECTS

The procedures described above can be used to develop a 24 hour prolactin profile (or a set of key levels of prolactin during certain key intervals) for individuals under clinical evaluation for therapy according to the present invention. Individuals that are expected to have an abnormal daily prolactin rhythm include those having been diagnosed as afflicted with at least one of the following conditions: obesity (i.e., more than 20% overweight, based on age, frame size and sex characteristics using tables such as the Metropolitan Life Insurance Company tables for standard weight for height and age), insulin-resistance, hyperglycemia, hyperinsulinemia, hyperlipidemia, or Type II diabetes. However, the present evaluation is not limited to such subjects.

The subjects to be considered for therapy should be euthyroid, i.e., have a total T3 level between about 90 and about 180 ng/dl, total T4 between about 4.5 and about 12 g/dl, and free-T4 between about 0.7 and about 1.9 g/dl. If not, T4 and/or T3 should be administered (preferably in the morning hours) prior to or concurrently with prolactin modulator administration. In other words, it is preferable to adjust the prolactin profile of an individual if his/her levels of T4 and/or T3 are normal. Thus, prior to adjusting the prolactin profile or levels of a subject through administration of a prolactin stimulator, or inhibitor, or both, it is preferred to determine that the subject is euthyroid. If the thyroid hormone levels in a subject are below normal (as determined with reference to the above normal values) T3 and/or T4 are, preferably, first administered to the subject until the plasma levels of these hormones are normal and prolactin stimulatory or inhibitory treatment is then begun. The thyroid hormone amount administered is the dosage required to bring the patient to a euthyroid condition; usually between about 25 and about 150 mcg per patient per day. If necessary to maintain adequate levels of T3/T4 throughout the period of administration of prolactin stimulator and/or inhibitor, T3/T4 can be continued along with the prolactin modulator therapy agents. Hyperthyroid subject should also receive treatment (via use of antithyroid agents or thyroid ablation) prior to prolactin modulator treatment.

Once a diurnal prolactin level profile has been developed for an individual, the profile is compared to the "normal" profile (e.g., the one generated as described in the previous section or to FIG. 1). A determination can then be made based on the following general criteria:

1. From about 07:00 h to about 22:00 h, i.e., during the flat and low level portion of the "normal" prolactin profile, at a given time point in the prolactin profile of the subject the (blood) prolactin value must not be higher than one SEM above the mean at the same time point (or higher than 2 SEM above the mean at one time point, or higher than one SEM above the mean at two different time points). This rule applies to exclude from a conclusion of "normal" all individual prolactin profiles that do not meet the above criteria, either because their prolactin is too high during the day or because their prolactin is too low during sleeptime, or both.

2. From about 22:00 h till about 07:00 h, i.e., during the rapid change (and sleeptime peak) of the normal daily prolactin profile, the individual's prolactin profile must first have a peak at about the same time or within two to six hours after sleep initiation as the "normal" prolactin peak for subjects in the same category (usually about 01:00) and must also be within one SEM of the normal healthy prolactin profile (preferably for two prolactin readings or alternatively within two SEM for at least one prolactin reading).

It should be noted that, based on clinical experience of the present inventors, adjusting high day time prolactin levels to normal or near normal values effects a significant improvement in the pathologies of the patients treated even if, as a result of the treatment, the night time prolactin peak is lessened. Therefore, consistent with this observation, observance of criterion 1 above takes priority over observance of criterion 2.

If only a set of key prolactin measurements are made for the subject being tested, the above criteria are applied as follows: if at any of the "day" time points at which key prolactin measurements have been made for the subject his/her prolactin level is higher than 1 SEM (and preferably 2 SEM) above the mean day time normal prolactin level at the same time point, then the subject has an abnormal day prolactin profile or rhythm; and if at any "night" time point for which a key prolactin level has been measured the prolactin level of the subject (taken during the key interval of 23:00–02:00) is lower than 1 SEM (and preferably 2 SEM) below the mean sleeptime normal prolactin level at the same time point, then the subject has an abnormal night prolactin profile or rhythm.

To determine if a subject has an aberrant prolactin profile the bedtime on the subject's prolactin profile should ideally be coincident with the bedtime on the profile of normal subjects. If this is not the case, the profile of the subject and the profile of normal individuals can be superimposed and one or the other can be shifted so that the sleep initiation time of the subject to be tested coincides with the sleep initiation time of normal healthy subjects.

DETERMINATION OF TREATMENT FOR AN AFFECTED SUBJECT

The information (prolactin profile and set of key prolactin levels) generated as described above is used to (a) identify the patients that are in need of an adjustment in their prolactin profile and (b) to determine the type and extent of adjustment required. In general, those individuals that are obese, hyperinsulinemic, hyperlipidemic, hyperglycemic and/or diabetic display abnormal prolactin profiles (or key prolactin levels) as compared to healthy individuals. Simply stated, by comparing a subject's prolactin profile (or key prolactin levels) with the standard prolactin profile, or corresponding healthy (normal) set of prolactin levels, it is possible to identify individuals afflicted with the abnormal conditions discussed above. By adjusting the abnormal prolactin profile of such individuals (either by administration of a prolactin inhibitor or a prolactin stimulator, or both) at the appropriate time of day and in the appropriate dosage (amount) it is possible to adjust such individuals' prolactin profile to conform (or at least approach) a normal profile. The amount and timing of administration of such dosages can be determined based upon information contained in the prolactin profiles (or key prolactin levels) discussed above.

An adjusted profile approaches a normal or healthy profile if all or a portion of the abnormal profile moves in the correct direction by at least 2 ng/ml. For example, if a human subject's abnormal prolactin level is 18 ng/ml between 07:00 and 10:00 and (after adjustment) it is reduced to 16 ng/ml during the same time period, the adjusted profile approaches the healthy profile. It is thus important to reduce the area under the daytime prolactin curve (typically by at least about 20%) and to avoid prolactin peaks during the day.

The treatment determination has three aspects: (a) choice of effect desired (i.e., choice of prolactin stimulator to increase prolactin levels, or prolactin inhibitor to reduce prolactin levels, or both to increase prolactin at night and to reduce prolactin during the day); (b) timing of (each) dose of administration; and (c) amount of (each) dose to be administered. For example, generally if the patient is initially diagnosed as requiring a prolactin inhibitor, he might initially receive 0.8–1.6 mgs per day of (preferably) accelerated release bromocriptine in a single dose (or in divided doses). The dosage might be adjusted after about 4 weeks of treatment e.g., at that time a fresh prolactin profile (or a set of key prolactin levels) would be taken and e.g., if the patient still had a high prolactin level he would receive an increased dosage of (preferably) an accelerated release prolactin inhibitor at the appropriate time of day. The time of administration might also be adjusted (depending on the patient's current prolactin profile or key prolactin levels), e.g., the time of bromocriptine administration would be changed.

The comparison of the individual prolactin profile (or levels) to the normal prolactin profile (or levels) will determine (a) and (b) in the preceding paragraph, as follows: If at any point during the "day" prolactin level is too high (whether or not it has a peak), administration of a prolactin inhibitor is required.

If the "night" prolactin profile lacks a peak or if its peak is not sufficiently pronounced, administration of a prolactin stimulator is required.

The preferred prolactin inhibitor (or dopamine agonist) is an accelerated release inhibitor, in particular an accelerated release composition containing bromocriptine as set forth in co-pending U.S. patent application Ser. No. 08/171,897 (now abandoned in favor of Rule 62 continuation application Ser. No. 08/600,487 now abandoned).

The preferred prolactin stimulator is metoclopramide.

Whether a 24-hour prolactin profile is generated for a subject to be treated, or only key prolactin levels are measured, the following more specific guidelines will generally be followed to initially determine bromocriptine administration timing, for a period of treatment of approximately 26 weeks:

a) Week 1 to Week 6. First Dosage: If any one of a patient's 07:00, 08:00, 16:00 or 19:00 prolactin levels is equal to or higher than 5.0 ng/ml for males or 7.0 ng/ml for females, then 0.8 mg of accelerated release bromocriptine is administered at 06:00 daily.

Second Dosage: Beginning in week 3, a second dosage containing 0.8 mg of accelerated release bromocriptine is also administered at 10:30 daily.

b) Week 7 to Week 12. First dosage: If any one of the 07:00, 08:00, 16:00, or 19:00 prolactin values is still equal to or higher than 5.0 ng/ml for males or 7.0 ng/ml for females, then 1.6 mg of accelerated release bromocriptine are administered at 06:00. Otherwise, 0.8 mg of accelerated release bromocriptine is administered at 06:00 daily.

Second Dosage: In addition, if the 19:00 prolactin level is less than or equal to 1.5 ng/ml for males or females then the second dosage of 0.8 mg of accelerated release bromocriptine is administered at 08:30 daily instead of at 10:30. If the 19:00 prolactin level is higher than 1.5 ng/ml for males and females, then the second dosage continues to administered at 10:30 daily.

If the 19:00 prolactin level is less than 1.0 ng/ml for males and females, then there is no administration of second dosage.

c) Week 13 to Week 26. For both first and second dosages the rules are the same set forth for Weeks 7–12, subject to the following:

(i) If either the 16:00 or 19:00 prolactin level is equal to or higher than 5.0 ng/ml for males or 7.0 ng/ml for females, then add an additional 0.8 mg of accelerated release bromocriptine to the first dosage, unless the patient is already receiving 2.4 mg of bromocriptine in total. In that case, add the additional 0.8 mg of accelerated release bromocriptine to the second dosage;

(ii) If the 19:00 prolactin level is lower than 1.5 ng/ml for males or females, then the second dosage time is adjusted by administering it 2 hours earlier; and (iii) If each of the 08:00, 16:00 and 19:00 prolactin levels is less than 1.0 ng/ml for males or females, then subtract 0.8 mg of accelerated release bromocriptine from the second dosage, or, if there is no second dosage, then subtract 0.8 mg of accelerated release bromocriptine from the first dosage. In the vast majority of patients, the first dosage must contain a minimum of 0.8 mg of accelerated release bromocriptine.

The time and amount schedules given above are intended as guidelines for bromocriptine administration and those skilled in the art can further adjust the precise timing and amount of bromocriptine administration based on the actual prolactin profile or key prolactin levels of a patient to be treated. For example, if a patient does not respond (or does not respond adequately) to a given dosage or dosages (e.g. 0.8 mg) it (or they) can be increased (e.g. to 1.6 mg).

When needed, metoclopramide (generally daily dosage range is 0.5–5.0 mg/person; preferred daily dosage range is 0.5–2.0 mg/person) can be administered once about one hour before bedtime. A prolactin stimulator in general is not administered unless the average prolactin level of the patient between 01:00 and 04:00 is at least 1 SEM (preferably based on two data points or at least 2 SEM if based on only one data point) lower than 8.0 ng/ml for males or 14 ng/ml for females. Furthermore, when the day time prolactin is too high a substantial clinical benefit will be realized by adjustment of the day time prolactin levels and the administration of a prolactin stimulator will not be required in most cases (although it may be desirable).

In general, the time at which an inhibitory agent other than bromocriptine, or stipulatory agent other than metoclopramide, is to be administered to a patient can be determined by ascertaining the time between administration of the agent and the time at which the agent exerts its maximum biological (i.e., stimulatory or inhibitory) effect. The time at which a stimulator has its maximum stimulating effect, (or when an inhibitor has its maximum inhibition effect) can be determined by administering the stimulatory or inhibitory drug to a patient with a known prolactin profile and then calculating the time that elapses between administration of the drug and exertion of the maximum effect on movement (either inhibition or stimulation) of the patient's (known) prolactin profile.

In fine tuning a subject's medication administration schedule, the rebound effect that administration of a prolactin inhibitor during the day might have in sleeptime prolactin levels of this subject should be taken into account. Conversely, the rebound effect that administration of a prolactin stimulator might have on prolactin levels during the subject's waking hours should also be considered. In this manner, and using the methodology of the foregoing guidelines, the time of administration for a particular inhibitor or stimulator can be determined using routine experimental procedures.

The precise time of modulator administration that will yield the most effective results in terms of efficacy of treatment in a given patient will depend upon the activity, pharmacokinetics, and bioavailability of a particular modulator, physiological conditions of the patient (including age, disease type and stage, physical condition, responsiveness to a given dosage and modulator), route of administration, etc. However, the above guidelines can be used as the basis for determining the optimum time of administration.

The foregoing are applicable for setting initial therapy regimens. In general a patient receives between about 3 and about 100 micrograms of bromocriptine per kilogram of body weight per day, and preferably between about 10 and 40 micrograms per kg of body weight per day. The exact dosage of prolactin inhibitor (or prolactin stimulator) required to achieve the optimum effect in terms of prolactin adjustment must be adjusted for each patient based upon the patient's drug sensitivity (i.e., response to drug) age, disease state and stage and physical condition. The patient is periodically reevaluated by measuring prolactin levels at predetermined intervals during a 24-hour period, preferably (or shorter period if necessary), the first such reevaluation typically occurring at the end of four weeks from the onset of therapy, and subsequent reevaluations occurring every 4 to 8 weeks during therapy and then every 3 months thereafter. Typical daily dosages of bromocriptine for humans on a per patient basis are 0.2–15 mg, preferably 0.8–8 mg.

Prolactin stimulators are normally administered within about 1 hour prior to retiring for the patient's normal sleep period.

Adjustments to the amount(s) of drug(s) administered and possibly to the time of administration may be made as described above based on these reevaluations.

Generally, adjustment of timing and amount of drug(s) is not considered necessary if the sleeptime prolactin peak during therapy is higher than normal as long as the peak value occurs at the right time, and the slopes of the peak are sharp (with normal values at each side of the normal peak).

The efficacy of a particular regimen on a particular patient and the adjustments (in dosage and timing) required, if any, can be determined by comparing the patient's re-evaluation prolactin profile or reevaluation key prolactin levels with the standard profile (or the "healthy" key profile levels).

In treating vertebrates, generally, dosages of the accelerated release prolactin inhibitor (bromocriptine) and/or stimulator (metoclopramide), respectively, are each given, generally once a day, generally over a period ranging from about 10 days to about 180 days, but treatment can continue indefinitely (if necessary or desired) for months or even years. The preferred prolactin inhibitor (accelerated release bromocriptine) is given daily at dosage levels ranging from about 3 micrograms to about 100 micrograms, preferably from about 10 micrograms to about 40 micrograms, per kg. of body weight, and the prolactin stimulator (metoclopramide) is given daily at dosage levels ranging from about 5 micrograms to about 200 micrograms, preferably from about 5 micrograms to about 100 micrograms, per kg. of body weight per day to modify, or alter, the prolactin profile (or the key prolactin level) and continued for a time sufficient to reset the circadian plasma prolactin rhythm, at which time treatment may be discontinued. If the subject suffers a relapse, treatment may be resumed.

In treating humans, in particular, the prolactin inhibitor (accelerated release bromocriptine) is generally given at daily dosage levels ranging from about 3 micrograms to about 100 micrograms, preferably from about 10 micrograms to about 40 micrograms, per kg. of body weight. The prolactin stimulator metoclopramide is generally given at daily dosage levels ranging from about 5 micrograms to about 50 micrograms, preferably from about 5 micrograms to about 20 micrograms, per kg. of body weight per day. (Per person daily dosages range of metoclopramide are typically 0.5 to 5.0 mg; preferably 0.5 to 2.0 mg.) Such treatment (using one or both types of drugs) is typically continued over a period of time ranging from about 10 days to usually about 180 days, resulting in modification and resetting of the lipid and glucose metabolism of the patient to that of a lean (i.e., normal) healthy person, at which time treatment may be discontinued. For some patients (e.g. patients in particularly poor physical condition, or those of an advanced age) it may not be possible to reset their prolactin rhythm within the above time periods and such patients may require a longer, or even continuous, treatment with prolactin stimulators and/or inhibitors. The dosage and timing information set forth above is designed for bromocriptine and metoclopramide and will have to be altered for other agents using the dosage and timing methodology disclosed herein.

In the practice of this invention, a prolactin-inhibiting compound, and a prolactin stimulator are administered daily to a subject preferably orally, or by subcutaneous, intravenous or intramuscular injection. Dermal delivery systems e.g., skin patches, as well as suppositories and other well-known systems for administration of pharmaceutical agents can also be employed.

Body fat deposits, inclusive of adipose, arterial wall and plasma fat, of an obese person will be reduced, leveled out and generally maintained (after the treatments of the present invention are discontinued) at that of a normal (lean) person, over an extended period of time. A subject that exhibits the effects of insulin resistance, hyperlipidemia or hyperinsulinemia and/or hyperglycemia, or both insulin resistance and hyperinsulinemia and/or hyperglycemia, treated with the prolactin inhibitor and/or a prolactin stimulator at the appropriate times of day discussed above, will become more sensitive to insulin (i.e., will have a lower insulin resistance), and the effects of hyperinsulinemia and/or hyperglycemia and related abnormal metabolic values will be reduced on a long term basis. Treatment generally lasts between about 10 and about 180 days on average in humans. The administration of the prolactin inhibitor (or dopamine agonist) and/or prolactin stimulator in this manner will thus reset the phase relations of the two neural oscillations and their various circadian expressions to alter metabolism on a long term basis (e.g., several years), if not permanently. In other words, the result of the timed daily dosages of the prolactin inhibitor (or dopamine agonist) and/or prolactin stimulator will be a long term reversal of the major pathologies generally associated with the development of Type II diabetes. Using the methods of the present invention, the levels of body fat stores, plasma insulin concentrations (including in patients oral hypoglycemic medications), insulin resistance, hyperglycemia, and blood pressure or all of these pathologies can be reduced on a long term basis by such treatment, or treatments, from the high levels often found in obese, hyperinsulinemic, hyperlipidemic and/or hyperglycemic persons to approach or conform to the much lower and much more desirable levels found in normal persons with normal insulin levels.

The following are non-limiting working examples of diagnosis, regimen determination and therapy according to the present invention:

Case Study 1: (130010)

Subject: male; 52 yrs; 294 lbs; 5 ft 6 in.

Pretreatment pathology:

(a) Obesity: 191% IBW (based on a standard Table, e.g., the standard table of Metropolitan Life Insurance Co. NY, N.Y. available from the company);

(b) Type II diabetes: fasting plasma glucose 164 mg; percent glycosylated hemoglobin 9.4% (measured by affinity chromatography); The normal morning fasting plasma glucose is between 80 and 120 mg percent (mg %).

The subject's 24-hour base (pre-therapy) prolactin profile is shown graphically as the dotted grey line in FIG. 1. It shows that the subject's prolactin was too high throughout the day and early evening. At 07:00, it was 13.2 ng/ml and at 08:00, 11.8 ng/ml; at 16:00 it was 9.9 ng/ml and at 19:00 it was 12.2 ng/ml. The subject was administered accelerated release bromocriptine as follows: Weeks 1 and 2: 1.6 mg at 05:00; weeks 3 and 4: 0.8 mg at 05:00 and an additional 0.8 mg at 10:00; Weeks 5–18: 1.6 mg at 05:00. A (reevaluation) prolactin profile was generated for the subject after 18 weeks and is graphically shown in FIG. 2 as the thin black line. The key prolactin values were 07:00 11.6 ng/ml; 08:00 9.5 ng/ml; 16:00 3.3 ng/ml and 19:00 6.5 ng/ml.

The improvements observed in this patient's prolactin levels after 12 weeks of treatment included significantly lower levels throughout most of the day and early evening.

The clinical benefits of treatment to this patient included reduction in glycosylated hemoglobin from a starting level of 9.4% to 7.6% after 18 weeks of treatment. The patient lost 18 pounds of body fat over 18 weeks; plasma cholesterol was reduced from 229 mg % to 180 mg %; triglycerides were reduced from 186 mg % to 122 mg %; fasting glucose was reduced from 164 mg % to 133 mg %; and oral glucose tolerance test results improved, over the treatment period.

Case Study 2: (130007)

Subject: male; 53 yrs; 203 lbs; 5 ft. 10 in.

Pretreatment pathology:

(a) Obesity: 130% IBW;

(b) Type II diabetes: fasting plasma glucose 168 mg %, glycosylated hemoglobin 7.5%.

Figure 3:
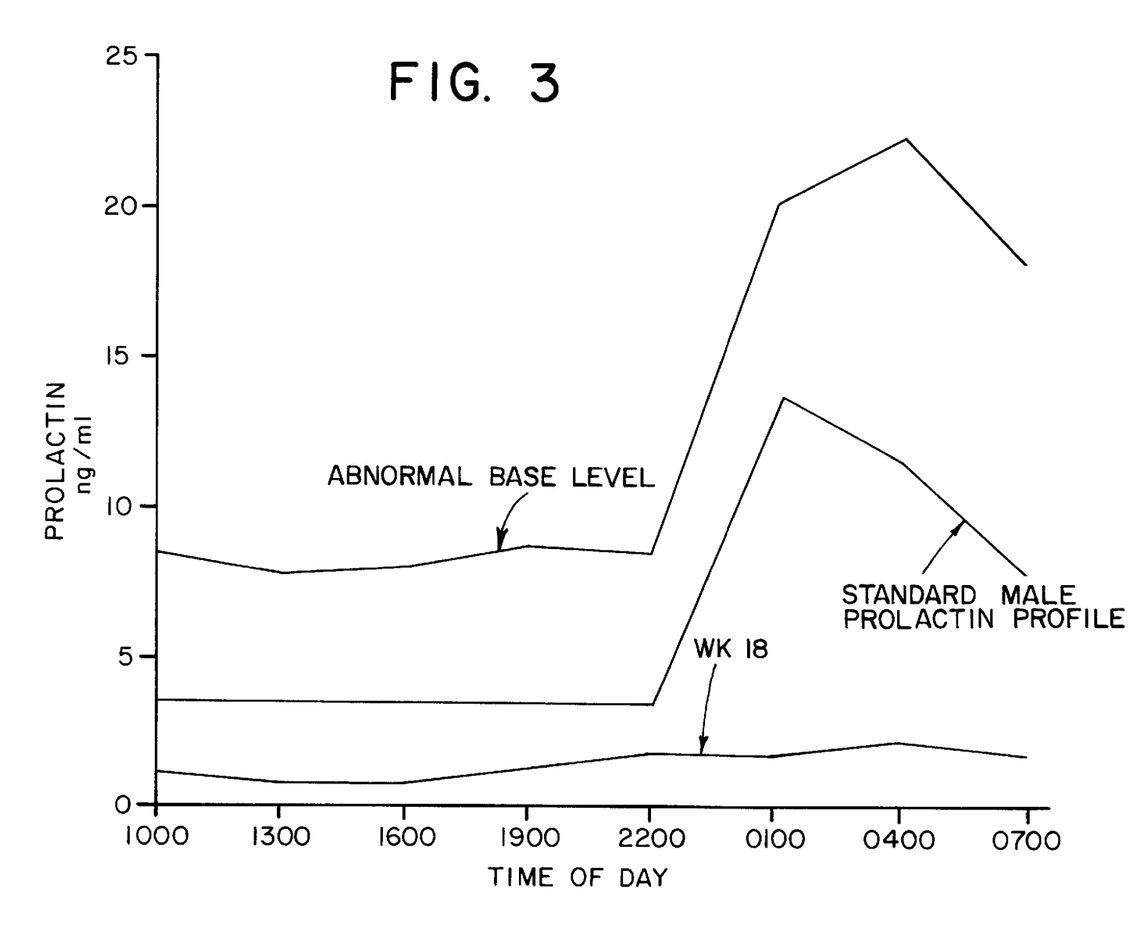
FIG. 3 is the same type of graphical superimposition as FIG. 2 for another male patient.

On initial evaluation, the subject had the prolactin profile shown in FIG. 3 as the dotted grey line. The day levels (particularly the 07:00 level) are too high: at 7:00, 18.2 ng/ml; at 8:00, 15.0 ng/ml; at 16:00, 8.1 ng/ml; and at 19:00, 8.8 ng/ml. The night time peak is also somewhat delayed. The patient was administered accelerated release bromocriptine as follows: Weeks 1 and 2: 1.6 mg at 08:30; Weeks 3 and 4: 1.6 mg at 08:00; Weeks 5 and 6: 0.8 mg at 08:30; Weeks 7–18: 1.6 mg at 05:00.

The second profile (the thin black line) taken after 18 weeks of treatment shows that the subject's prolactin profile was very sensitive to bromocriptine. The day time levels were significantly reduced. However, the night time levels were also reduced below normal. Prolactin levels were as follows: at 7:00, 1.9 ng/ml; at 8:00, 1.7 ng/ml; at 16:00, 0.9 ng/ml; and at 19:00, 1.5 ng/ml.

The clinical benefits of treatment to this patient included reduction in glycosylated hemoglobin from a starting level of 7.5% to 6.1%. The patient lost 23 pounds of body fat; the patient's OGTT test showed considerable improvement, with the area under the glucose curve declining by approximately 30%; and fasting glucose was reduced from 168 mg % to 133 mg %, over the course of treatment.

The data show that metabolic states are regulated at least to a clinically significant degree in part by an interaction of circadian neuroendocrine rhythms. This hypothesis proposes that the daily rhythms of cortisol and prolactin are individual expressions of two separate circadian systems and that the phase relations of these two systems can be reset. Thus, in a hamster model it has been found that the 0-hour relation resets the circadian oscillations into a pattern that maintains the lean, insulin sensitive state and the 12-hour relation permits retention of a pattern that maintains the obese, insulin resistant state. Another important addition of the present study is that the effects of timed injections of a prolactin inhibiting dopamine agonist, or other prolactin inhibiting compound, are long lasting. Apparently once reset, the phase relation of the two circadian oscillations tends to maintain its altered pattern.

Changes in the phase relations of two circadian neuroendocrine oscillations are evidenced by changes in the phase relations of their circadian expressions. This expectation is fulfilled respecting plasma glucocorticosteroid and prolactin rhythms. In several species examined, the phase relations of the two hormone rhythms differ in lean and fat animals.

The phase relation between the circadian rhythm of plasma insulin concentration and the rhythm of lipogenic responsiveness to insulin is shown to differ in lean and fat animals. Whereas the daily interval of lipogenic responsiveness remains near light onset, the phase of the insulin rhythm varies markedly. The peak concentration of insulin, e.g., occurs near light onset in obese female hamsters held on short day-lengths. That is, the daily peaks of the lipogenic stimulus (i.e., insulin) and the lipogenic response to insulin coincide in fat animals and not in lean animals.

It is apparent that various modifications and changes can be made without departing from the spirit and scope of this invention.

What is claimed is:

1. A method for normalizing the daily prolactin rhythm in a first subject having an abnormal prolactin daily rhythm which comprises the steps of:

comparing a prolactin profile obtained from predetermined prolactin levels of said first subject to a prolactin profile of healthy subjects of the same species; and adjusting the prolactin profile of said first subject to generally conform to or approach the prolactin profile of healthy subjects, thereby normalizing said rhythm, wherein said adjusting step comprises at least one of:
administering to said first subject a first predetermined amount of a prolactin inhibitor at a first predetermined time during waking hours at which the subject's prolactin level is higher than said healthy subjects' prolactin level by more than 1 SEM; and
administering to said first subject a second predetermined amount of a prolactin stimulator at a second predetermined time prior to a time point in said prolactin profile of said first subject at which said subject's sleeptime prolactin level is lower than 1 SEM below said healthy subjects' prolactin level.

2. A method for determining adjustments that will cause an abnormal daily prolactin rhythm of a patient to conform to or approach a healthy subject's daily prolactin rhythm, which comprises:

a. comparing a prolactin profile obtained from predetermined prolactin levels of a patient to a predetermined standard prolactin profile for healthy human subjects of the same sex as said patient;

b. determining that said patient should be administered a prolactin inhibitor when at any time point during waking hours the patient's prolactin level exceeds the prolactin level of healthy subjects at the same time point by more than 1 SEM;

c. selecting at least one time for administration to said patient of said prolactin inhibitor that is no later than the time at which the prolactin level of said patient during waking hours reaches its highest waking hours level; and d. selecting the amount of said prolactin inhibitor to be administered to said patient so that the prolactin profile of said patient during waking hours generally conforms to or approaches the prolactin profile of healthy subjects during waking hours, thereby causing the patient's abnormal daily prolactin rhythm to conform to or approach said healthy subject' daily prolactin rhythm.

3. The method of claim 2 wherein said prolactin inhibitor is bromocriptine and said subject is a human.

4. The method of claim 3 wherein said bromocriptine is administered at least once between 06:00 and 12:00 h.

5. The method of claim 4 wherein said bromocriptine is administered at a total daily amount within the range of 0.8–8.0 mg.

6. The method of claim 5 wherein at least a portion of said bromocriptine is administered at 6:00 AM.

7. A method for determining adjustments that will cause an abnormal daily prolactin rhythm of a first subject to conform to or approach the daily prolactin rhythm of healthy subjects, comprising:

a. comparing a prolactin profile obtained from predetermined prolactin levels of a first subject to a predetermined standard prolactin profile for healthy subjects;

b. determining that said first subject is in need of administration of a prolactin stimulator by ascertaining that the prolactin level of said first subject at any time point during sleeptime is at least 1 SEM lower than the prolactin level of said healthy subjects at the same time point;

c. selecting the timing of said administration to said first subject to be prior to the time at which the sleeptime prolactin level reaches its peak in healthy subjects; and d. selecting an amount of said prolactin stimulator to be administered to said first subject such that the prolactin profile of said first subject during sleeptime generally conforms to or approaches the prolactin profile of said healthy subjects during sleeptime, thereby causing said first subject's abnormal daily prolactin rhythm to conform to or approach the daily prolactin rhythm of healthy subjects.

8. A method for normalizing the daily prolactin rhythm in a first subject having an abnormal prolactin daily rhythm which comprises the steps of:

comparing a set of key predetermined prolactin levels of said subject to a corresponding set of prolactin levels of healthy subjects of the same species at the same time points as said key levels; and adjusting the prolactin rhythm of said first subject to generally conform to or approach the prolactin rhythm of said healthy subjects and thereby normalize said rhythm, wherein said adjusting step comprises at least one of:
administering to said first subject a prolactin inhibitor if at least one key predetermined prolactin level of said first subject during waking hours is higher than 1 SEM above the corresponding prolactin level of said healthy subjects; and
administering to said first subject a prolactin stimulator if at least one key prolactin level of said first subject during night time is lower than 1 SEM below the corresponding prolactin level of said healthy subjects.

9. The method of claim 8 wherein said prolactin inhibitor is bromocriptine and said subject is a human.

10. The method of claim 9 wherein said bromocriptine is administered at least once between 06:00 and 13:00 h.

11. The method of claim 10 wherein said bromocriptine is administered at a total daily amount within the range of 0.8–8.0 mg.

12. The method of claim 11 wherein at least a portion of said bromocriptine is administered at 6:00 AM.

13. A method for determining adjustments that will cause an abnormal daily prolactin rhythm of a patient to conform to or approach a healthy subject's daily prolactin rhythm, which comprises:

a. comparing a set of key predetermined prolactin levels of said patient to corresponding standard prolactin levels at the same time points for healthy human subjects of the same sex as said patient;

b. determining that said patient should be administered a prolactin inhibitor when at least one key prolactin level of said patient exceeds the corresponding prolactin level of healthy subjects at the same time point by more than 1 SEM;

c. selecting at least one time for administration to said patient of said prolactin inhibitor that is between 06:00 h and 12:00 h; and d. selecting the amount or amounts of said prolactin inhibitor to be administered to said patient so that at least one key prolactin level of said patient during waking hours will conform to or approach the corresponding prolactin level of healthy subjects, thereby causing the patient's abnormal prolactin daily rhythm to conform to or approach a healthy subject's daily prolactin rhythm.

14. A method for determining adjustments that will cause an abnormal daily prolactin rhythm of a first subject to conform to or approach the daily prolactin rhythm of a healthy subject, comprising:

a. comparing a set of key predetermined prolactin levels of said first subject to a set of predetermined prolactin levels obtained from a standard prolactin profile for healthy subjects;

b. determining that said first subject is in need of administration of a prolactin stimulator by ascertaining that a least one key prolactin level of said first subject during sleeptime is at least 1 SEM lower than the prolactin level of said healthy subjects during sleeptime;

c. selecting the timing of said administration to said first subject to be prior to the time at which the sleeptime prolactin level reaches its peak in healthy subjects; and d. selecting an amount of said prolactin stimulator to be administered to said first subject such that at least one key prolactin level of said first subject during sleeptime is no lower than 1 SEM below the corresponding prolactin level of said healthy subjects at the same time point, thereby causing the first subject's abnormal daily prolactin rhythm to conform to or approach the daily prolactin rhythm of a healthy subject.

15. A method for determining whether a vertebrate test subject having a daily prolactin rhythm is in need of administration of one or more prolactin modulators that will cause an abnormal daily prolactin rhythm to approach or conform to a healthy subject's daily prolactin rhythm, which comprises the steps of:

(a) measuring a blood prolactin level of the vertebrate test subject at least once at a predetermined time point during a day time interval selected from at least one of early morning and early evening;

(b) comparing the measured prolactin level of said test subject to a corresponding predetermined standard prolactin level for healthy subjects of the same species at the same day time point; and (c) determining that the test subject should be administered a prolactin inhibitor to decrease daytime prolactin levels of the subject, and thereby cause the test subject's prolactin rhythm to conform to or approach a healthy subject's prolactin rhythm, in the event that:

(i) said prolactin level of said test subject obtained from a single measurement in one of said intervals exceeds the corresponding standard prolactin level of healthy subjects at the same day time point by more than 2 standard errors of the mean, or (ii) each of at least two of said prolactin levels of said test subject measured in one of said intervals exceeds the corresponding prolactin level of healthy subjects at the same day time point by more than 1 standard error of the mean.

16. The method of claim 15 further comprising the steps of:

(d) measuring a blood prolactin level of the test subject at least once at a predetermined time point during the night to obtain a night prolactin level;

(e) comparing said night prolactin level of the test subject to a corresponding predetermined standard night prolactin level for healthy subjects of the same species at the same night time point; and (f) determining that the test subject should be administered a prolactin stimulator to increase night time prolactin levels of the subject, and thereby cause the test subject's prolactin rhythm to further conform to or approach a healthy subject's prolactin rhythm, in the event that;

(i) said night prolactin level of said test subject obtained from a single measurement is lower than the corresponding standard night prolactin level of healthy subject is by more than 2 standard errors of the mean, or (ii) each of at least two of said night prolactin levels of said test subject is lower than the corresponding standard night prolactin level of healthy subjects by more than 1 standard error of the mean.

17. The method of claim 16 wherein in steps (b) and (e), the healthy subjects are of the same sex as the test subject.

18. The method of claim 15 which comprises measuring said blood prolactin level twice in early morning.

19. The method of claim 15 which comprises measuring said blood prolactin level twice in early evening.

20. The method of claim 15 which comprises measuring said blood prolactin level twice in early morning and twice in early evening.

21. The method of claim 15 which comprises measuring said blood prolactin level once in early morning and once in early evening.

22. The method of claim 15 wherein said human subject suffers from Type II diabetes.

23. The method of claim 15 wherein said human subject suffers from obesity.

24. The method of claim 15 wherein said human subject suffers from hyperlipidemia.

25. A method for identifying in a group of human subjects being tested a test subject in need of administration of one or more prolactin modulators that will cause an abnormal daily prolactin rhythm of said test subject to approach or conform to a healthy subject's daily prolactin rhythm, which comprises the steps of:

(a) measuring the blood prolactin levels of said subjects being tested at least once at a predetermined time point during a day time interval selected from one or more of early morning and early evening;

(b) comparing a prolactin level of each subject being tested to a corresponding standard prolactin level for healthy subjects of the same species at the same day time point; and (c) determining that a test subject should be administered a prolactin inhibitor to decrease daytime prolactin levels of the test subject, and thereby cause the test subject's abnormal daily prolactin rhythm to conform to or approach a healthy subject's daily prolactin rhythm, in the event that:
  (i) a prolactin level of said test subject obtained from a single measurement in one of said intervals exceeds the corresponding standard prolactin level of healthy subjects at the same day time point by more than 2 standard errors of the mean, or
  (ii) each of at least two prolactin levels of said test subject measured in one of said intervals exceeds the prolactin level of healthy subjects at the same day time point by more than 1 standard error of the mean.

26. The method of claim 25 further comprising the steps of:
  (d) measuring a blood prolactin level of said test subject at least once at a predetermined time point during the night to obtain a night prolactin level;
  (e) comparing said night prolactin level of said test subject to a corresponding predetermined standard night prolactin level for healthy subjects of the same species at the same night time point; and
  (f) determining that the test subject should be administered a prolactin stimulator to increase night time prolactin levels of the subject, and thereby cause the test subject's abnormal daily prolactin rhythm to further conform to or approach a healthy subject's daily prolactin rhythm, in the event that:
    (i) a night prolactin level of said test subject obtained from a single measurement is lower than the corresponding standard night prolactin level of healthy subjects by more than 2 standard errors of the mean, or
    (ii) each of at least two night prolactin levels of said test subject is lower than the corresponding standard night prolactin level of healthy subjects by more than 1 standard error of the mean.

27. The method of claim 25 wherein in steps (b) and (e), the healthy subjects are of the same sex as the test subject.

28. The method of claim 25 which comprises measuring said blood prolactin level twice in early morning.

29. The method of claim 25 which comprises measuring said blood prolactin level twice in early evening.

30. The method of claim 25 which comprises measuring said blood prolactin level twice in early morning and twice in early evening.

31. The method of claim 25 which comprises measuring said blood prolactin level once in early morning and once in early evening.

32. The method of claim 25 wherein said subjects being tested suffer from Type II diabetes.

33. The method of claim 25 wherein said subjects being tested suffer from obesity.

34. The method of claim 25 wherein said subjects being tested suffer from hyperlipidemia.

35. A method for determining whether a human subject is in need of administration of one or more prolactin modulators that will cause an abnormal daily prolactin rhythm of said human subject to approach or conform to a healthy subject's daily prolactin rhythm, which comprises the steps of:
  (a) collecting blood samples from a human subject at least once at a predetermined time point during a time interval selected from at least one of early morning and early evening;
  (b) measuring the prolactin content of each of said samples;
  (c) plotting the prolactin content of each of said samples against the time at which said sample was collected to generate a daytime key prolactin level data point;
  (d) comparing said daytime key prolactin level data point to a corresponding predetermined standard prolactin level for healthy subjects at the same day time point; and
  (e) determining that the human subject should be administered a prolactin inhibitor to decrease daytime prolactin levels of the subject, and thereby cause an abnormal daily prolactin rhythm of the human subject to conform to or approach a healthy subject's daily prolactin rhythm, in the event that:
    (i) said prolactin level of said human subject obtained from a single measurement in one of said intervals exceeds the standard prolactin level of healthy subjects at the same day time point by more than 2 standard errors of the mean, or
    (ii) each of at least two prolactin levels of said human subject measured in one of said intervals exceeds the prolactin level of healthy subjects at the same time point by more than 1 standard error of the mean.

36. The method of claim 35 further comprising the steps of:
  (f) collecting a blood sample from the human subject at least once at a predetermined time point during the night;
  (g) measuring the prolactin content of each of said samples to obtain a night prolactin level;
  (h) comparing each of said night prolactin levels of said human subject to a predetermined standard night prolactin level for healthy subjects at the same night time point; and
  (i) determining that the human subject should be administered a prolactin stimulator to increase night time prolactin levels of the subject, and thereby cause the human subject's abnormal daily prolactin rhythm to further conform to or approach a healthy subject's daily prolactin rhythm, in the event that:
    (i) said night prolactin level of said human subject obtained from a single measurement is lower than the corresponding standard night prolactin level of healthy subjects by more than 2 standard errors of the mean, or
    (ii) each of at least two night prolactin levels of said human subject is lower than the corresponding standard night prolactin level of healthy subjects by more than 1 standard error of the mean.

37. The method of claim 35 wherein in steps (d) and (h), the healthy subjects are of the same sex as the human subject.

38. The method of claim 35 which comprises measuring said blood prolactin level twice in early morning.

39. The method of claim 35 which comprises measuring said blood prolactin level twice in early evening.

40. The method of claim 35 which comprises measuring said blood prolactin level twice in early morning and twice in early evening.

41. The method of claim 35 which comprises measuring said blood prolactin level once in early morning and once in early evening.

42. The method of claim 35 wherein said human subject suffers from Type II diabetes.

43. The method of claim 35 wherein said human subject suffers from obesity.

44. The method of claim 35 wherein said human subject suffers from hyperlipidemia.

45. A method for determining whether a vertebrate subject having a daily prolactin rhythm is in need of administration of one or more prolactin stimulators that will cause an abnormal daily prolactin rhythm to approach or conform to a healthy subject's daily prolactin rhythm, which comprises the steps of:
   (a) measuring the blood prolactin level of a vertebrate subject at least once at a predetermined time point during the night to obtain a night prolactin level;
   (b) comparing said night prolactin level of said vertebrate subject to a corresponding predetermined standard night prolactin level for healthy subjects of the same species at the same night time point; and
   (c) determining that the vertebrate subject should be administered a prolactin stimulator to increase night time prolactin levels of the subject in the event that:
      (i) said night prolactin level of the vertebrate subject obtained from single measurement is lower than the corresponding standard night prolactin level of healthy subjects by more than 2 standard errors of the mean, or
      (ii) each of at least two of said night prolactin levels of said vertebrate subject is lower than the corresponding standard night prolactin level of healthy subjects by more than 1 standard error of the mean.

46. A method for normalizing the daily prolactin rhythm in a first subject having an abnormal prolactin daily rhythm in that the subject has at least one of the following:
   (i) at least one key prolactin level at any time point during sleeptime that is at least 1 SEM lower than the prolactin level of healthy subjects at the same time point; and
   (ii) at least one key prolactin level at any time point during waking hours that exceeds the corresponding prolactin level of healthy subjects at the same time point by more than 1 SEM;
   the method comprising at least one of:
      administering to said first subject a first predetermined amount of a prolactin inhibitor at least once between 06:00 and 12:00 h; and
      administering to said first subject a second predetermined amount of a prolactin stimulator at about one hour before said subject's bedtime
   thereby normalizing said daily prolactin rhythm in said first subject.

47. The method of claim 46 wherein said prolactin inhibitor is bromocriptine and said first subject is a human.

48. The method of claim 47 wherein said bromocriptine is administered at a total daily amount within the range of 0.8–8.0 mg.

49. The method of claim 48 wherein at least a portion of said bromocriptine is administered at 6:00 AM.

* * * * *